(12) United States Patent
Stellon et al.

(10) Patent No.: US 7,390,315 B2
(45) Date of Patent: Jun. 24, 2008

(54) MOLDED TROCAR LATCH

(75) Inventors: Gene Stellon, Southington, CT (US); David C. Racenet, Litchfield, CT (US); Ralph A. Stearns, Bozrah, CT (US); Adam Lehman, Wallingford, CT (US)

(73) Assignee: Tyco Healthcare Group, LP, North Haven, CT (US)

( * ) Notice: Subject to any disclaimer, the term of this patent is extended or adjusted under 35 U.S.C. 154(b) by 595 days.

(21) Appl. No.: 10/349,524

(22) Filed: Jan. 24, 2003

(65) Prior Publication Data
US 2004/0147949 A1 Jul. 29, 2004

Related U.S. Application Data

(63) Continuation of application No. PCT/US01/24943, filed on Aug. 8, 2001.

(60) Provisional application No. 60/223,811, filed on Aug. 8, 2000.

(51) Int. Cl.
*A61M 5/178* (2006.01)
(52) U.S. Cl. .................................. 604/164.07
(58) Field of Classification Search .............. 606/185, 606/167, 170, 172, 174; 604/164.01, 164.02, 604/164.03, 164.08
See application file for complete search history.

(56) References Cited

U.S. PATENT DOCUMENTS

| | | | |
|---|---|---|---|
| 4,535,773 A | 8/1985 | Yoon | |
| 4,902,280 A | 2/1990 | Lander | |
| 5,030,206 A | 7/1991 | Lander | |
| 5,066,288 A | 11/1991 | Deniega et al. | |
| 5,104,382 A | 4/1992 | Brinkerhoff et al. | |
| 5,114,407 A | 5/1992 | Burbank | |
| 5,116,353 A | 5/1992 | Green | |
| 5,152,754 A | 10/1992 | Plyley et al. | |
| 5,215,526 A | 6/1993 | Deniega et al. | |
| 5,248,298 A | 9/1993 | Bedi et al. | |
| 5,263,937 A | 11/1993 | Shipp | |
| 5,290,243 A | 3/1994 | Chodorow et al. | |
| 5,295,993 A | 3/1994 | Green | |
| 5,312,354 A | 5/1994 | Allen et al. | |

(Continued)

FOREIGN PATENT DOCUMENTS

EP 0617 924 B1 10/1994

(Continued)

OTHER PUBLICATIONS

European Search Report for corresponding European Patent Application-EP01962001 - Date of Mailing Jul. 11, 2006 (3 pages).

*Primary Examiner*—Kevin T. Truong

(57) ABSTRACT

A molded trocar latch apparatus for locking a safety shield in position is described. The molded latch includes a trocar housing and a shield. The housing has a first monolithically formed cap and a monolithically formed base. A latch mechanism, including a slider and a latch, may be monolithically formed with either the base or the cap of the housing. The slider and the latch are operatively connected to move the latch between a locked and an unlocked position. The latch in the locked position is configured to engage a ledge on the shield and at least stop further proximal movement of the shield that could unintentionally expose the blade of the trocar.

15 Claims, 5 Drawing Sheets

U.S. PATENT DOCUMENTS

| | | |
|---|---|---|
| 5,314,417 A | 5/1994 | Stephens et al. |
| 5,318,585 A | 6/1994 | Guy et al. |
| 5,338,305 A | 8/1994 | Plyley et al. |
| 5,350,393 A | 9/1994 | Yoon |
| 5,356,421 A | 10/1994 | Castro |
| 5,364,372 A | 11/1994 | Danks et al. |
| 5,370,625 A | 12/1994 | Shichman |
| 5,374,252 A | 12/1994 | Banks et al. |
| 5,387,197 A | 2/1995 | Smith et al. |
| 5,399,167 A | 3/1995 | Deniega |
| 5,431,635 A | 7/1995 | Yoon |
| 5,437,643 A | 8/1995 | Transue |
| 5,441,513 A | 8/1995 | Roth |
| 5,462,532 A | 10/1995 | Gresl |
| 5,538,509 A | 7/1996 | Dunlap et al. |
| 5,549,564 A | 8/1996 | Yoon |
| 5,578,053 A | 11/1996 | Yoon |
| 5,591,190 A * | 1/1997 | Yoon .......................... 606/185 |
| 5,626,598 A | 5/1997 | Roth |
| 5,645,556 A | 7/1997 | Yoon |
| 5,645,557 A | 7/1997 | Yoon |
| 5,669,885 A | 9/1997 | Smith |
| 5,772,660 A | 6/1998 | Young et al. |
| 5,827,315 A | 10/1998 | Yoon |
| 5,860,996 A | 1/1999 | Urban et al. |
| 5,980,493 A | 11/1999 | Smith et al. |
| 6,017,356 A * | 1/2000 | Frederick et al. ............ 606/185 |
| 6,036,711 A | 3/2000 | Mozdzierz et al. |
| 6,099,544 A | 8/2000 | Wolf et al. |
| 6,319,266 B1 | 11/2001 | Stellon et al. |

FOREIGN PATENT DOCUMENTS

| | | |
|---|---|---|
| WO | WO 94/22508 | 10/1994 |
| WO | WO 02/11605 A2 | 2/2002 |

\* cited by examiner

MOLDED TROCAR LATCH

CROSS REFERENCE TO RELATED APPLICATIONS

This application is a continuation of PCT/US01/24943, filed Aug. 8, 2001, which claims the benefit of U.S. Provisional Application No. 60/223,811, filed Aug. 8, 2000.

BACKGROUND

1. Technical Field

The present disclosure relates to a surgical trocar assembly and, in particular, to a trocar assembly having an integral latch mechanism which locks a protective shield of the trocar assembly in a fixed position and prevents retraction within the housing to the trocar assembly. Subject matter related to this application is disclosed in commonly assigned U.S. patent application Ser. No. 09/526,837 filed Mar. 16, 2000, entitled "Modular Trocar System and Methods of Assembly", and U.S. application Ser. No. 5,352,274 entitled "SAFETY TROCAR", filed Dec. 7, 1994 by Green, now U.S. Pat. No. 5,486,190, the contents of which are incorporated herein by reference.

2. Background of Related Art

Trocars are sharp pointed instruments used to puncture a body cavity. Generally, a trocar includes an obturator having a sharp obturator lip for penetrating the cavity wall and a protective sleeve in which the obturator is coaxially positioned. The trocar further includes a trocar sleeve or cannula. Once the body cavity has been punctured by the trocar, the obturator is typically removed from the cannula, thereby leaving the cannula in place extending into the body cavity. Endoscopic or laparoscopic procedures are then performed with surgical instruments, e.g., laparoscopes, dissectors, graspers, staplers introduced through the cannula.

Commercially available safety trocars includes a spring loaded safety shield which is adapted to cover the obturator tip once the body cavity has been entered so as to provide an increased level of protection to internal structures from puncture or laceration. Other available safety trocars incorporate latching mechanisms having complex trigger and linking arrangement for locking and unlocking the protective sleeve. For example, a convenient location of the trigger on the trocar may require at least one intermediary linking mechanism to operatively connect the trigger with the locking member. The intermediary linking mechanism moves the locking member for the locking or unlocking of the shield in response to an operator's movement of the trigger. Latch mechanisms also generally require multiple bias members to ensure the positioning and the desired interrelation of the components such as the blocking member and linking mechanism. These configurations often require tightly controlled tolerances and are complex and time consuming to assemble. Additional complications include the manual adjusting of the interrelated components, such as the biased elements, after manufacturing in order to ensure the desired operational quality and reliability of the device.

A continuing need exists for a trocar latch mechanism that is monolithically molded as an assembly requiring a minimal number or even no additional components. A continuing need also exists for a trocar latch mechanism that reduces manufacturing costs by minimizing the need for manual post manufacturing adjusting of the latch mechanism.

SUMMARY

A molded trocar latch apparatus is provided, the apparatus including a trocar housing and a shield. The housing includes a first monolithically formed portion or cap and a second monolithically formed portion or base. A latch mechanism is monolithically formed from one of the base and cap of the housing. The latch mechanism includes a slider and a latch. The slider is movable between a first position and a second position by an operator. The slider and the latch are operatively connected to move the latch between a locked and an unlocked position. The shield includes a cam positioned to disengage the slider from the latch. Upon disengagement, the latch is configured to return to the locked position and the first position.

The presently disclosed molded trocar latch, together with attendant advantages, will be best understood by reference to the following detailed description in conjunction with the figures below.

BRIEF DESCRIPTION OF THE DRAWINGS

Preferred embodiments of the present disclosure are described herein with reference to the drawings wherein.

DETAILED DESCRIPTION

Figure 1:
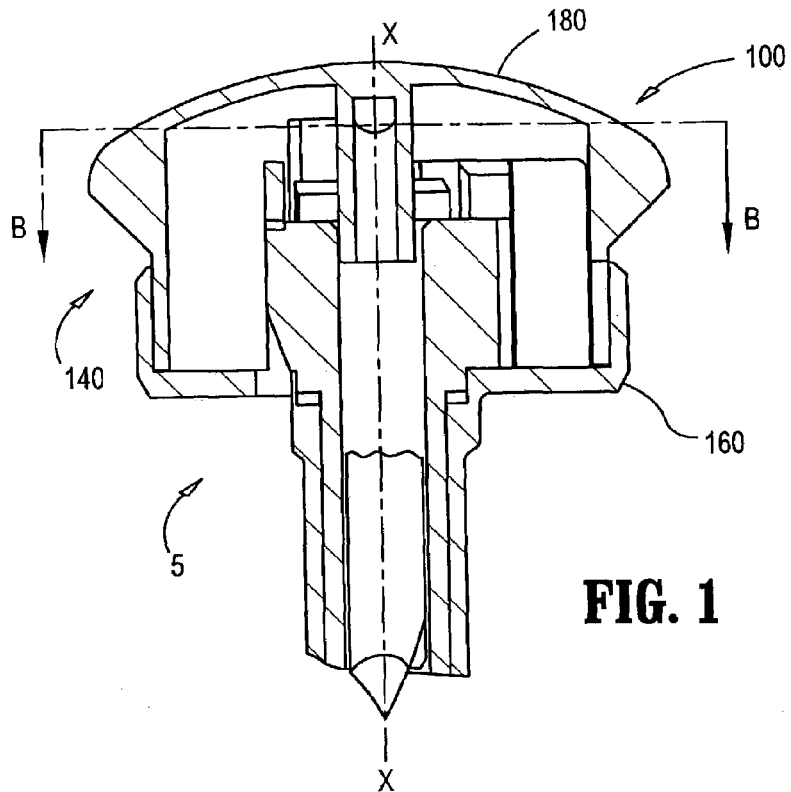
FIG. 1 is a cross sectional side view of a trocar assembly incorporating the latch mechanism of the present disclosure, illustrating a molded latch mechanism utilizing a cross beam latch.
Figure 2:
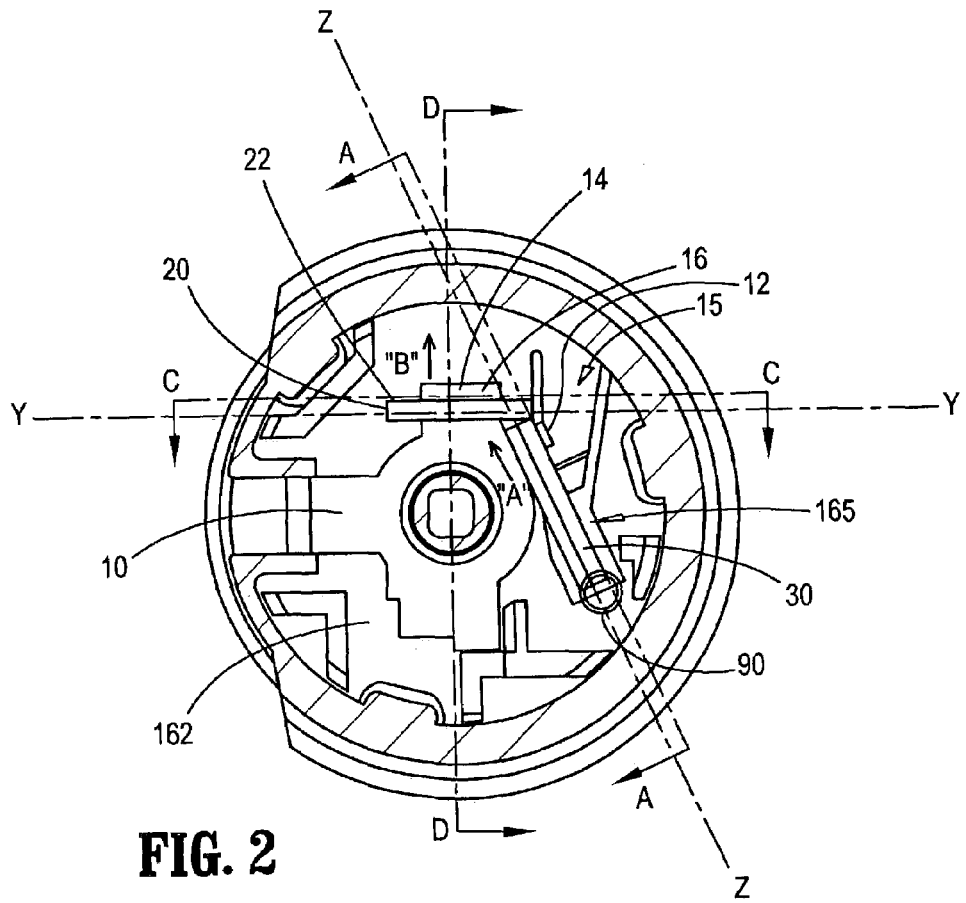
FIG. 2 is a cross sectional top view of the latch mechanism of FIG. 1 along lines B-B.

Referring initially to FIGS. 1-4, a trocar molded latch system 100 is configured for selectively positioning a latch mechanism 15 in a locked position and an unlocked position with a shield 10. In the locked position, shield 10 is physically positioned over a trocar blade or a sharpened obturator edge, for example, to prevent accidental lacerations. The unlocked position allows shield 10 to be moved proximally, against a bias, to expose the blade of the trocar during operational use such as, for example, during a percutaneous penetration of a patient. Trocar molded latch system 100 includes a housing 140, a base or a second portion 160, a cap or a first portion, shield 10, and latch mechanism 15. Base 160 and cap 180 are molded from a medical grade plastic as monolithic assemblies and then integrated into housing 140 of trocar latch system 100. Base 160 may be monolithically formed with the cannula of trocar assembly 5 or in the alternative, molded trocar latch 100 may be configured to connect with a cannula housing of trocar 5 as a removable assembly. Latch mechanism 15 includes a latch 20 and an actuating mechanism 30. Shield 10 is a movable assembly having a proximal end including a cam 12 and ledge 14. Trocar assembly 5 defines a central longitudinal axis-X. A bias 90, such as a compression spring, may be provided to assist shield 10 in backing off or moving distally from within housing 140. Bias 90 may be a separate assembly or formed as part of the base or cap or in combinations thereof In a first preferred embodiment, latch 20 is a cantilevered beam structure 22 monolithically formed with and extending proximally from a floor 162 of trocar base 160. Cantilevered beam 22 has two parallel beams or legs 24 and 26 that extend axially in a proximal direction, parallel with the longitudinal axis-X. A cross member 28, approximately perpendicular to the longitudinal axis is positioned on the proximal ends of legs 24 and 26. The locked position for cantilevered beam 22 is when legs 24 and 26 are approximately aligned with the central longitudinal axis.

Inside edges 21 and 23 of legs 24 and 26, respectively, a distal edge 27 of cross member 28, and floor 162 define a hole 25. Hole 25 is configured and dimensioned for receiving and engaging ledge 14 of shield 10 and thereby blocking further proximal movement of shield 10. Ledge 14 extends generally perpendicular to and radially from the surface of shield 10. Ledge 14 has a modified block shape with a flat planar proximal end 16 extending radially from the tubular surface of shield 10 and a distally tapered distal end 18. Legs 24 and 26 in combination with cross beam 28 define an axis-Y perpendicular to the central longitudinal axis-X. Cantilevered beam 22 is configured as a flexible structure biased to the locked or first position as a result of its materials of construction and structural shape.

A slider or actuating mechanism 30 is also monolithically formed with base 160 and is positioned at least partially in a slot 165 defined by floor 162. Slider 30, in this first preferred embodiment, has a generally right angled cantilevered beam configuration 32 having a beam or leg 34 aligned with the longitudinal axis-X and a cross beam 36 perpendicular to leg 34. The distal end of leg 34 has a rounded tip 31 that extends through slot 165 and is positioned at least partially distal to base 160. Slider 30 is connected to base 160 by a member 38 which is also configured as an area or point of flexure or pivoting. Leg 34 and cross beam 36 define an axis-Z perpendicular to longitudinal axis-X. Cross beam 36 has a tip 37 in apposition with cantilevered beam 22 when slider 30 is in the first position. Slider 30 is configured as a flexible structure biased to the locked or first position as a result of its materials of construction and structural shape and moveable between the first position and a second position wherein in the second position slider 30 has engaged latch 20 and repositioned latch 20 to the unlocked position.

Slider 30 is configured to pivot or flex along the direction of axis-Z against its inherent bias to intersect with cantilevered beam 22. Similarly, cantilevered beam 22 is configured to flex or pivot against its inherent bias about axis-Y. In this preferred embodiment, slider 30, moving along axis-Z, is configured to physically contact cantilevered beam 22, positioned along axis-Y, at a relative angle of approximately 115 degrees. The relative angle between the slider and latch can be varied in this embodiment through a range of approximately 75 degrees in any direction from a line perpendicular to the axis-Y and axis-X.

In operation, molded latch system 100 is in the locked position when shield ledge 14 is positioned in hole 25 and distal edge 27 of cantilevered beam 22 is engaging the proximal side 16 of shield ledge 14 precluding further proximal movement of shield 10. Molded latch system 100 is moved from the locked position to the unlocked position by an operator displacing actuating tip 31 in a generally proximal direction thereby pivoting slider 30 in the direction of axis-Z to directly engage tip 37 with cross beam 28. The displacement of tip 37 drives cross beam 28 to pivotally rotate cantilevered beam 22 about axis-Y and for cross beam 28 to be sufficiently displaced in the direction of arrow "A" to intersect with slider 30 such that latch 20 is driven radially outward in the direction of arrow "B" and out of contact with ledge 14, freeing shield 10 to move proximally and expose the blade of the trocar. This is the unlocked position of latch 100.

The proximal movement of shield 10 during operational use, such as during a percutaneous penetration, moves shield cam 12 from a first position at least partially distal to slider 30, to a second position proximal to slider 30. The translation of shield cam 12 between the first and second position contacts and repositions cross beam 36 of slider 30 in a radially direction away from shield 10 to displace slider 30 from being in apposition with cantilevered beam 22. When slider 30 is placed in the second position by an operator to reposition cantilevered beam 22 to the unlocked position, the contact of shield cam 12 with cross beam 36 disengages slider 30 from cantilevered beam 22. Cantilevered beam 22, as a result of its bias, then returns to the locked position and is prepared to engage ledge 14 and block further proximal movement of shield 10.

Alternatively, when slider 30 is released by the operator, the inherent bias in slider 30 will return it to the first position, removing the displacing force against cantilevered beam 22. Cantilevered beam 22 being similarly biased, then returns to the locked position. Thus, once tip 31 is released, molded trocar latch 100 is automatically returned as a result of its bias to the locked position and is prepared to engage and block proximal movements of shield 10 that would expose the obturator blade.

In FIGS. 5-9, a second embodiment of trocar molded latch system 200 includes a housing 240, base or second portion 260, cap or first portion 280, a shield 110, and a latch mechanism 115. Base 260 and cap 280 are molded from a medical grade plastic as monolithic assemblies and then integrated into housing 240 of trocar latch system 200. Latch mechanism 115 includes a latch 120 and an actuating mechanism 130. Shield 110 is a movable assembly having a proximal end including a cam 112 and ledge 114. Trocar assembly 50 defines a central longitudinal axis-X. A bias 190, such as a compression spring, may be provided to assist shield 110 in backing off or moving distally from within housing 240.

In the second preferred embodiment, latch 120 is an elongate cantilevered beam 122 defining an axis transverse to the longitudinal axis and monolithically formed with cap 280. Latch 120 includes a proximal end 123 connected to an interior wall 182 of cap 280 and extending in a distal direction to a distal end or tip 121. Tip 121 is positioned in apposition with shield 10 to block shield ledge 114 from any further proximal movement beyond tip 121. Tip 121 is in a locked position when it is directly contacting ledge 114 and shield 110 is blocked from retracting into housing 240. Cantilevered beam 122 is configured as a generally axially rigid structure in the direction of the longitudinal axis of beam 122, but has a controlled degree of flexibility in a direction perpendicular to the longitudinal axis of beam 122 to accommodate displacement from slider 30. Cantilevered beam 122 is biased to the locked position as a result of its materials of construction and structural shape.

Slider or actuating mechanism 130 is monolithically formed with base 260 and is positioned at least partially in a slot 265 defined by floor 262, and movable between a first position and a second position by an operator. Slider 130, in this first preferred embodiment, has a generally inverted "U" shaped cantilevered beam configuration 132 having a first beam 134 aligned with and a second beam 135 at least partially aligned with the longitudinal axis-X. Beams 134 and 135 are connected by a cross beam 136. The distal end of first leg 134 has a rounded tip 131 that extends through a slot 265 in base 260 and is positioned at least partially distal to base 260. Second beam 135 has a first portion 138 generally aligned with the longitudinal axis and a second portion 139 transverse to the longitudinal axis. Slider 130 is connected to base 260 through second beam 135 which is at least partially configured as an area or point of flexure or pivoting for slider 130. Leg 134, leg 135, and cross beam 136 define an axis-Z perpendicular to longitudinal axis-X. Cross beam 136 and portion 138 have an edge or and an inside corner between portion 139 positioned at least partially in apposition with cantilevered beam 122 when slider 130 is in the first position. Slider 130 is configured as a flexible structure biased to the locked position as a result of its materials of construction and structural shape.

Slider 130 is configured to pivot or flex along an axis-Z in the direction of arrow "C" against its inherent bias from the first position to intersect with and displace cantilevered beam 122. Similarly, cantilevered beam 122 is configured to flex or pivot against its inherent bias in the direction of arrow "C" to an unlocked position clear of ledge 114 when slider 130 is in the second position.

In operation, molded latch system 200 is in the locked position when proximal side 16 shield ledge 114 is positioned abutting tip 121 of cantilevered beam 122 precluding further proximal movement of shield 10. Molded latch system 200 is moved from the locked position to the unlocked position by an operator displacing actuating tip 131 in a generally proximal direction thereby pivoting slider 130 in the direction of axis-Z to directly engage edge 137 with beam 122 in the vicinity of tip 121. The displacement of tip 121 by edge 137 pivotally rotates or flexes cantilevered beam 122 about proximal end 123 sufficiently to displace tip 121 in the direction of arrow "C", generally aligned with axis-Z, to clear ledge 114, freeing shield 110 to move proximally and expose the trocar blade. This is the unlocked position of latch 200.

The continued proximal movement of shield 110 during operational use, such as during a percutaneous penetration, positions shield cam 112 proximal to slider 130. When shield cam 112 moves distally, it then intersect with cross beam 136 of slider 130 such that cross beam 136 is driven radially outward in the direction of arrow "D" and out of contact with cantilevered beam 122. Cantilevered beam 122, as a result of its bias, then returns to the locked position and is prepared to engage ledge 14 and block further proximal movement of shield 110.

Alternatively, when slider 130 is released by the operator, the inherent bias in slider 130 returns slider 130 to the first position, removing the displacing force against cantilevered beam 122. Cantilevered beam 122 being similarly biased, then returns to the locked position abutting shield 110. Thus, once tip 131 is released, molded trocar latch 200 is automatically returned as a result of its bias to the latched position and is prepared to engage and block proximal movements of shield 110 that would expose the obturator blade.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. For example, the molded geometry of individual components in the embodiments of the present disclosure, such as the slider and latch, can vary in origin from the base or the cap. Similarly, the geometry of the configuration of the ledge and cam of the shield depend upon on the specific design requirements of a given application of the molded trocar latch system. Further, the trocar housing or portions thereof may be configured as a removably and replaceable assembly with connections suitable for coupling with the trocar cannula.

Figure 3:
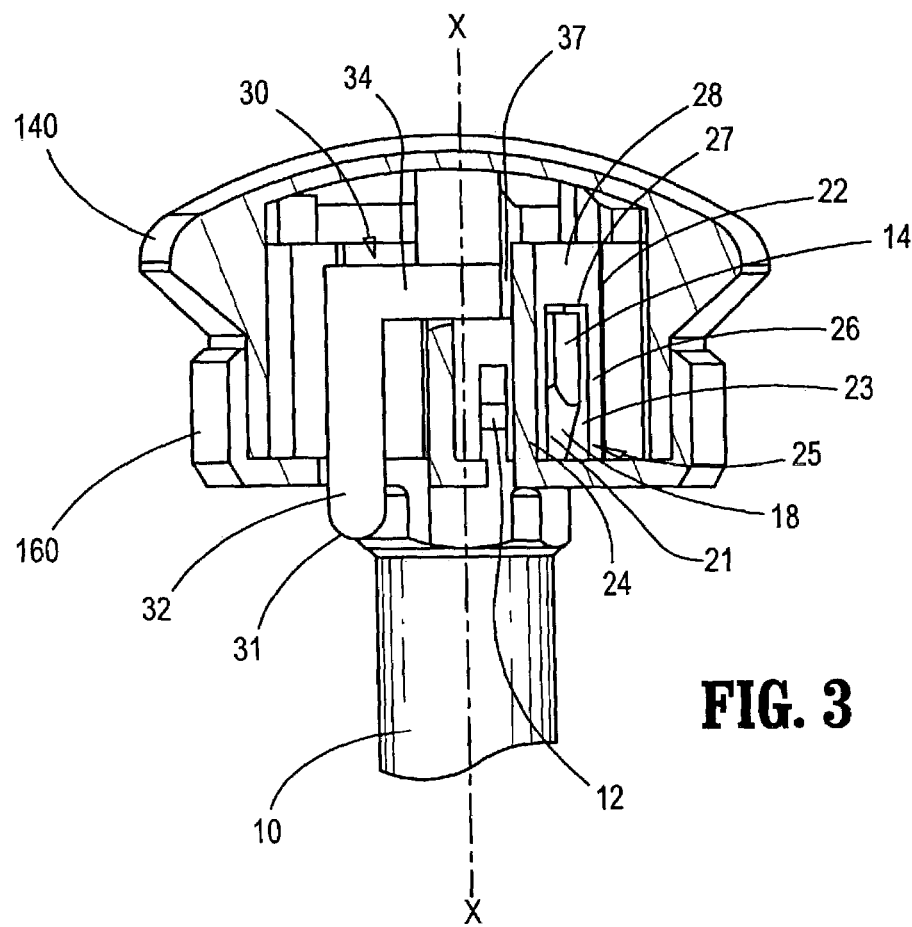
FIG. 3 is a cross sectional side view of FIG. 2 along lines C-C showing the slider.
Figure 4:
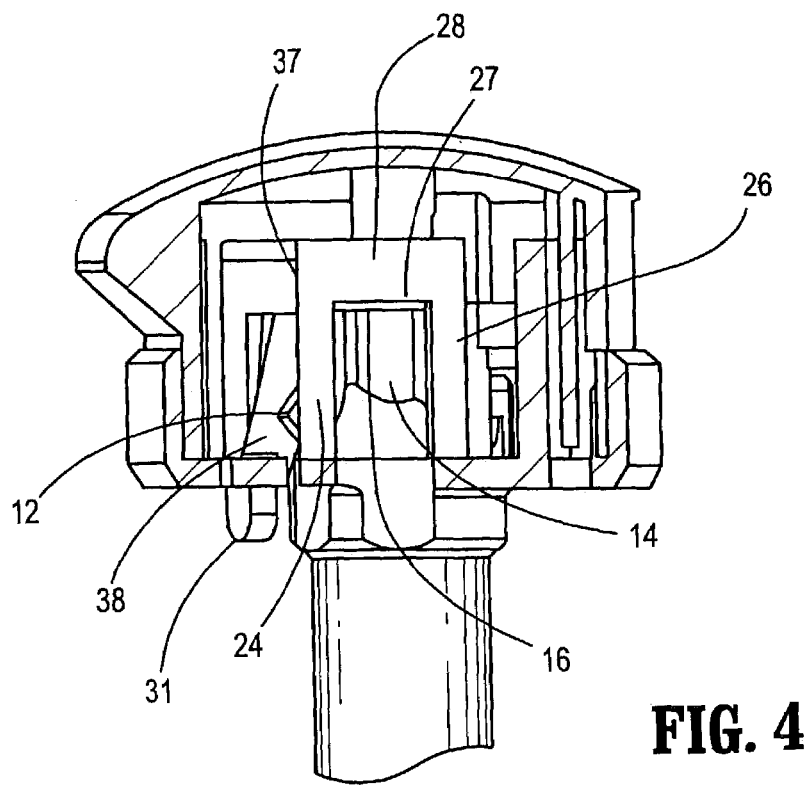
FIG. 4 is a cross sectional side view of FIG. 2 along lines D-D.
Figure 5:
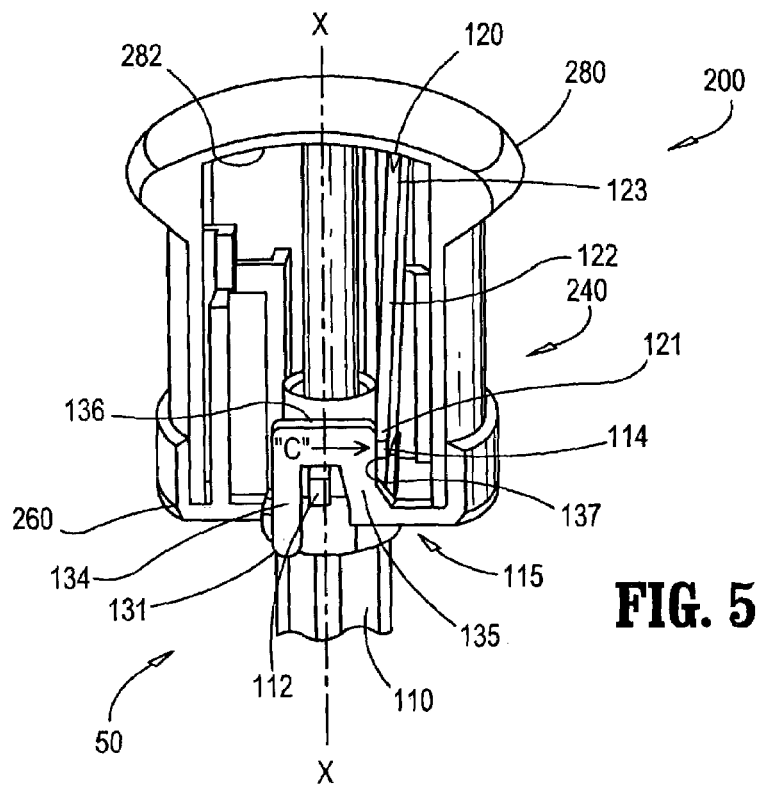
FIG. 5 is a cross sectional perspective side view of the second embodiment of the molded trocar latch mechanism utilizing an elongate cantilevered beam molded trocar latch constructed in accordance with the present disclosure.
Figure 6:
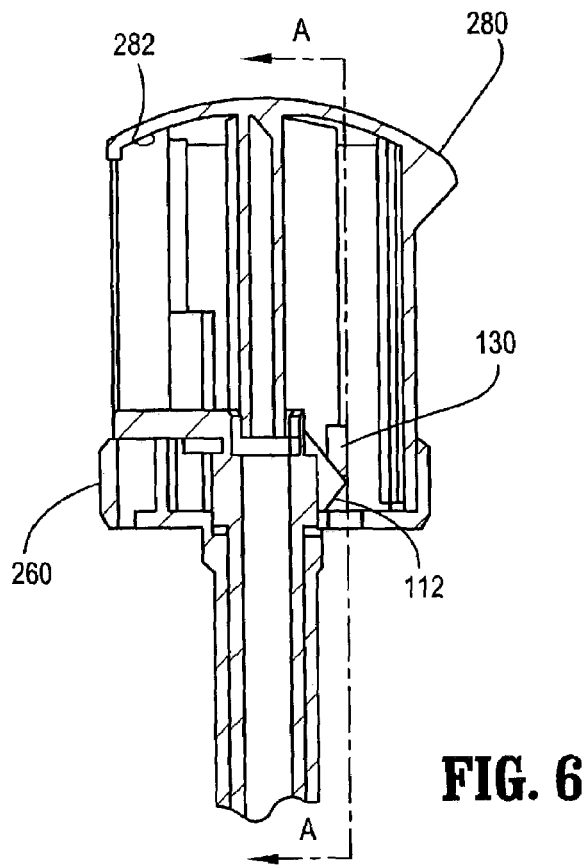
FIG. 6 is a second cross sectional side view of the elongate cantilevered beam molded trocar latch of FIG. 5.
Figure 7:
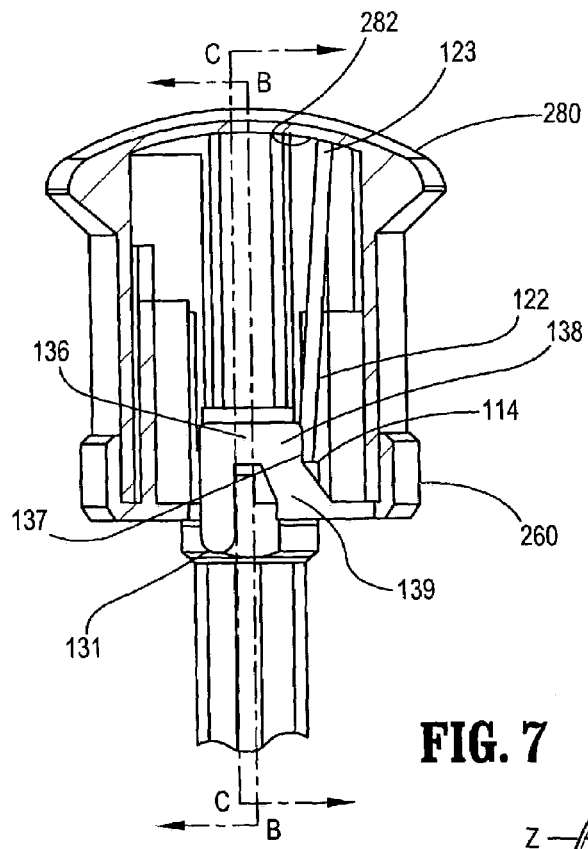
FIG. 7 is a cross sectional side view of FIG. 6 along lines C-C.
Figure 9:
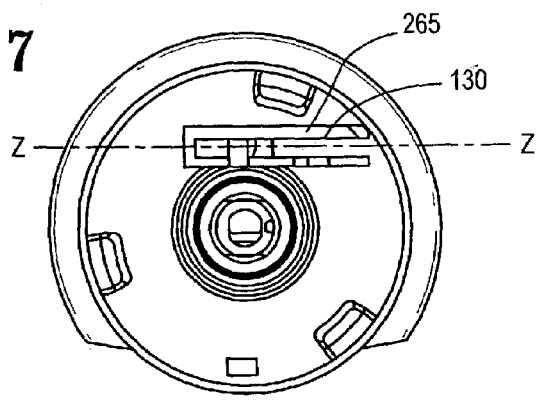
FIG. 9 is a simplified top view of the elongate cantilevered beam molded trocar latch mechanism showing the slide and the clearance cut around the slides.
Figure 8:
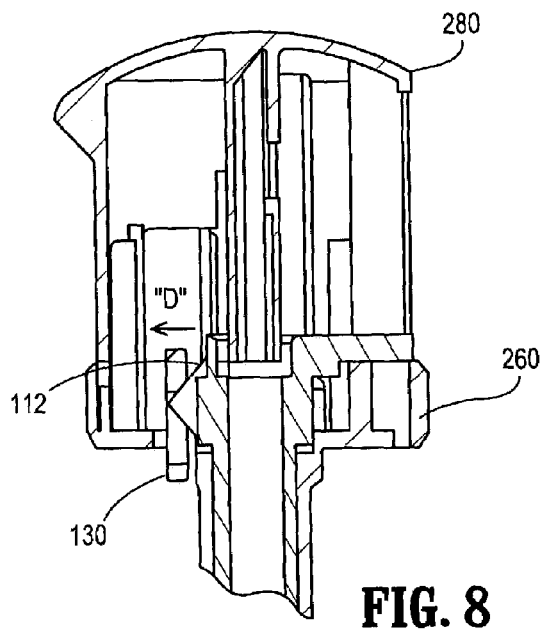
FIG. 8 is a cross-sectional side view of FIG. 7 along lines B-B.
Figure 10:
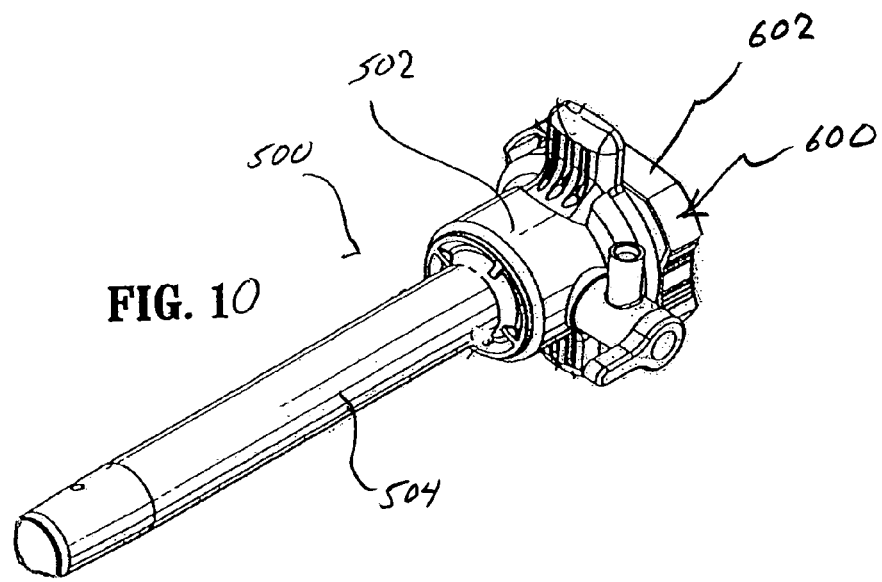
FIG. 10 is a perspective view of a cannula assembly and seal assembly for use with the trocar assembly of FIG. 1.
Figure 11:
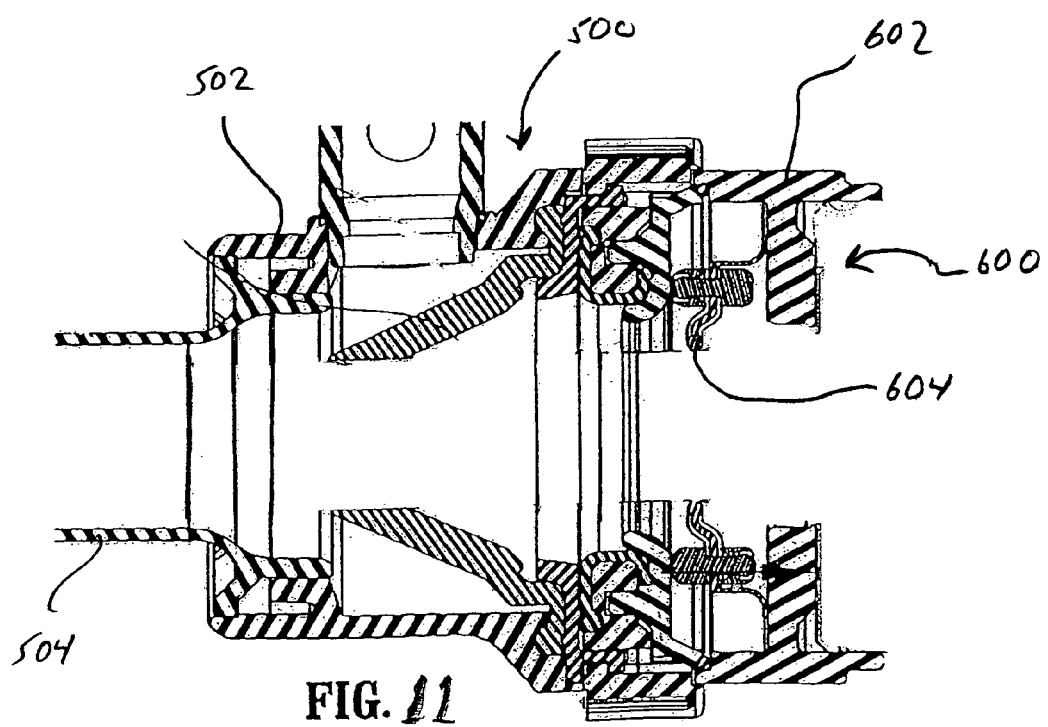
FIG. 11 is a partial side cross-sectional view of the cannula assembly and the seal assembly of FIG. 10.

FIGS. 10-11 illustrate a cannula and seal assembly for use with the trocar assembly. Specifically, cannula assembly 500 includes cannula housing 502 and cannula sleeve 504 extending from the cannula housing 502. Seal assembly 600 is mounted to cannula assembly 500 and includes a seal housing 602 and a seal member 604. Seal assembly 600 may be a component if cannula assembly. In use, the obturator of FIGS. 1 and 3 is introduced within the cannula assembly 500 and seal assembly 600, and advanced until base 160 of the obturator assembly mates with housing 602 of the seal assembly 604. During mating, beam 32 of slider 30 engages the proximal surface 606 of seal housing 602 which causes the slides 30 to flex and release the latch 20 in the manner discussed hereinabove.

It is thus understood that various modifications can be made to the various embodiments of the present invention without departing from its spirit and scope. Therefore the above description should not be construed as limiting the invention, but merely as presenting preferred embodiments of the invention. All such changes and modifications are intended to be included within the scope of the appended claims.

What is claimed is:

1. A surgical trocar, which comprises:
   a cannula having a cannula housing and a cannula sleeve extending from the cannula housing, the cannula sleeve having a longitudinal opening; and
   an obturator at least partially positionable within the cannula, the obturator including:
   an obturator housing;
   an obturator shaft extending from the obturator housing and defining a proximal end adjacent the housing and a distal end adapted to penetrate tissue;
   a shield positioned about the obturator shaft and adapted for longitudinal movement relative to the housing;
   a latch member monolithically formed with the housing and operatively engageable with the shield, the latch member being moveable from an initial position securing the shield in a first longitudinal position relative to the housing to a release position permitting the shield to move to a second longitudinal position relative to the housing in response to a counter force applied against the shield during engagement of the shield with tissue;
   a slider member monolithically formed with the housing and operatively coupled with the latch member, the slider member adapted for movement to cause corresponding movement of the latch member to the release position; and
   a release leg operatively coupled to the slider member, the release leg dimensioned to extend distally beyond the housing, the release leg being positioned to engage the cannula housing upon mating of the obturator housing and the cannula housing whereby a generally proximally directed force applied by the cannula housing on the release leg causes displacement of the release leg and movement of the latch member to the release position.

2. The trocar according to claim 1 wherein the release leg is monolithically formed with the slider member.

3. The trocar according to claim 1 wherein the obturator housing includes a housing base, the latch member and the slider extending from the housing base.

4. The trocar according to claim 3 wherein the release leg extends through an opening in the housing base.

5. The trocar according to claim 4 wherein the latch member is normally biased to the initial position thereof.

6. The trocar according to claim 5 wherein the latch member includes a locking surface adapted to securely engage a corresponding locking ledge of the shield when in the initial position thereof thereby substantially preventing longitudinal movement of the shield to the second longitudinal position.

7. The trocar according to claim 6 wherein the latch member is adapted for pivotal movement relative to the housing base to move from the initial position to the release position in response to actuation of the slider member whereby the locking surface of the latch member releases the locking ledge of the shield.

8. The trocar according to claim 3 wherein the slider member is adapted to pivot relative to the housing base to move the latch member to the release position thereof.

9. The trocar according to claim 8 wherein the slider member is normally biased to a position corresponding to the initial position of the latch member.

10. The trocar according to claim 1 wherein the housing includes a housing cap adapted for connection to the housing base.

11. A surgical trocar, which comprises:
   a cannula having a cannula housing and a cannula sleeve extending from the cannula housing, the cannula sleeve having a longitudinal opening; and
   an obturator at least partially positionable within the cannula, the obturator including:
   an obturator housing defining a longitudinal axis;
   an obturator shaft extending from the housing and having a distal penetrating tip;
   a shield mounted about the obturator shaft and adapted for longitudinal movement relative to the obturator shaft;
   a latch member disposed within the housing and operatively engageable with the shield, the latch member being moveable from an initial position securing the shield in a first longitudinal position relative to the obturator shaft to a release position permitting the shield to move to a second longitudinal position relative to the obturator shaft to expose the penetrating tip in response to a counterforce applied to the shield upon advancement of the shield within tissue;
   a slider member monolithically formed with the housing and operatively coupled with the latch member, the slider member adapted for movement to cause corresponding movement of the latch member to the release position; and
   a release leg operatively coupled to the slider member, the release leg dimensioned to extend distally beyond the housing and being positioned to engage the cannula housing upon mating of the housing and the cannula housing whereby a generally proximally directed force applied by the cannula housing on the release leg causes displacement of the release leg and movement of the latch member to the release position.

12. The trocar according to claim 11 including a release leg operatively coupled to the slider member, the release leg dimensioned to extend distally beyond the housing and being adapted for displacement to cause actuation of the slider member and movement of the latch member to the release position.

13. The trocar according to claim 11 wherein the release leg is monolithically formed with the slider member.

14. The trocar according to claim 11 wherein the latch member is monolithically formed with the housing.

15. The trocar according to claim 14 wherein the latch member is normally biased toward the initial position thereof.

* * * * *